United States Patent [19]

Huene

[11] Patent Number: 5,531,792
[45] Date of Patent: Jul. 2, 1996

[54] BONE PLUG FIXATION ASSEMBLY, EXPANSIBLE PLUG ASSEMBLY THEREFOR, AND METHOD OF FIXATION

[76] Inventor: Donald R. Huene, 201 N. Valeria, Fresno, Calif. 93701

[21] Appl. No.: 261,111

[22] Filed: Jun. 14, 1994

[51] Int. Cl.⁶ .................................. A61F 2/08; A61F 2/28
[52] U.S. Cl. .................................. 623/16; 623/13; 606/60; 606/62; 606/63; 606/95; 411/24; 411/55; 411/80
[58] Field of Search ................................ 623/13, 16; 606/95, 606/72, 73, 60, 62, 63; 411/24, 26, 55, 80

[56] References Cited

U.S. PATENT DOCUMENTS

| Re. 34,293 | 6/1993 | Goble et al. | 623/13 |
|---|---|---|---|
| 2,100,570 | 11/1937 | Saleh | 411/24 |
| 2,562,419 | 4/1948 | Ferris | 81/55 |
| 3,846,846 | 11/1974 | Fischer | 3/1 |
| 4,011,602 | 3/1977 | Rybicki et al. | 3/1.9 |
| 4,262,665 | 4/1981 | Roalstad et al. | 606/62 |
| 4,447,915 | 6/1984 | Weber | 623/16 |
| 4,708,132 | 11/1987 | Silvestrini | 128/92 |
| 4,744,793 | 6/1988 | Parr et al. | 623/13 |
| 4,789,284 | 12/1988 | White | 411/55 |
| 4,870,957 | 10/1989 | Goble et al. | 128/92 |
| 4,963,144 | 10/1990 | Huene | 606/73 |
| 5,019,080 | 5/1991 | Hemer | 606/73 |
| 5,037,422 | 8/1991 | Hayhurst et al. | 606/72 |
| 5,092,891 | 3/1992 | Kummer et al. | 606/62 |
| 5,094,563 | 3/1992 | Carletti | 403/194 |
| 5,129,902 | 7/1992 | Goble et al. | 606/65 |
| 5,161,916 | 11/1992 | White et al. | 405/259.6 |
| 5,176,682 | 1/1993 | Chow | 606/72 |
| 5,306,301 | 4/1994 | Graf et al. | 623/13 |
| 5,324,308 | 6/1994 | Pierce | 606/72 |

FOREIGN PATENT DOCUMENTS

| 1322067 | 2/1963 | France | 411/80 |
|---|---|---|---|
| 1368021 | 6/1964 | France | 411/24 |
| 0662082 | 5/1979 | U.S.S.R. | 606/63 |
| 1109142 | 8/1984 | U.S.S.R. | 606/63 |
| 0343992 | 3/1931 | United Kingdom | 411/24 |

*Primary Examiner*—David H. Willse
*Assistant Examiner*—Bruce E. Snow
*Attorney, Agent, or Firm*—Joseph W. Berenato, III

[57] ABSTRACT

An expansible bone plug assembly comprises a first member closed by a substantially planar surface at one end thereof, the member having a cylindrical outer surface. A central bore extends through the planar surface, and a plurality of longitudinally directed radially extendable fingers form part of the first member. A second member is closed by a hemispherical surface at one end thereof, and has a cylindrical outer surface. A plurality of longitudinally directed radially extendable fingers form part of the second member. The second member fingers are interdigitated with the first member fingers, and bear against the first member and the first member fingers bear against the second member. An axially extensible and retractable compression member extends through the bore and is engaged with the second member for causing the first and second members to be drawn together when the compression member is retracted, so that the fingers of the first and second members are thereby caused to extend radially outwardly.

17 Claims, 2 Drawing Sheets

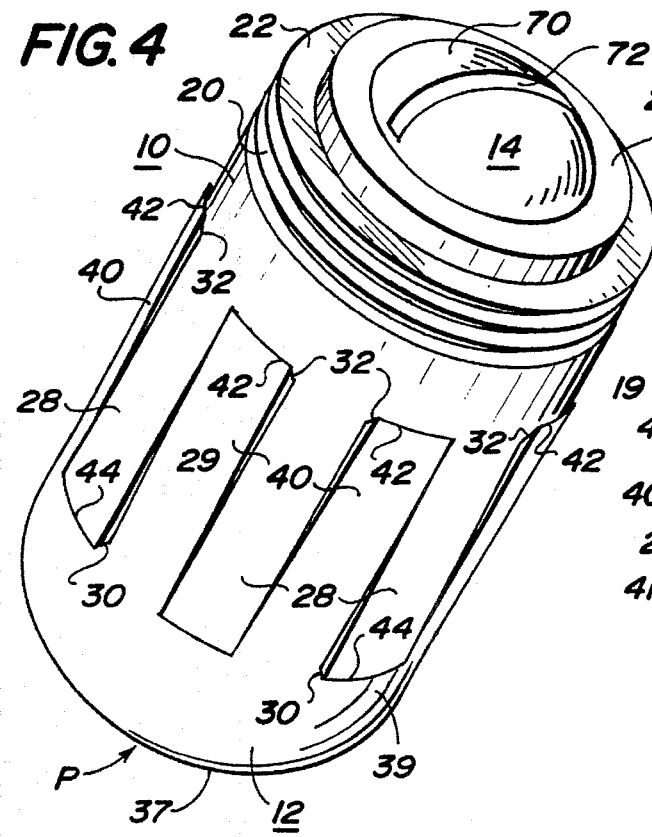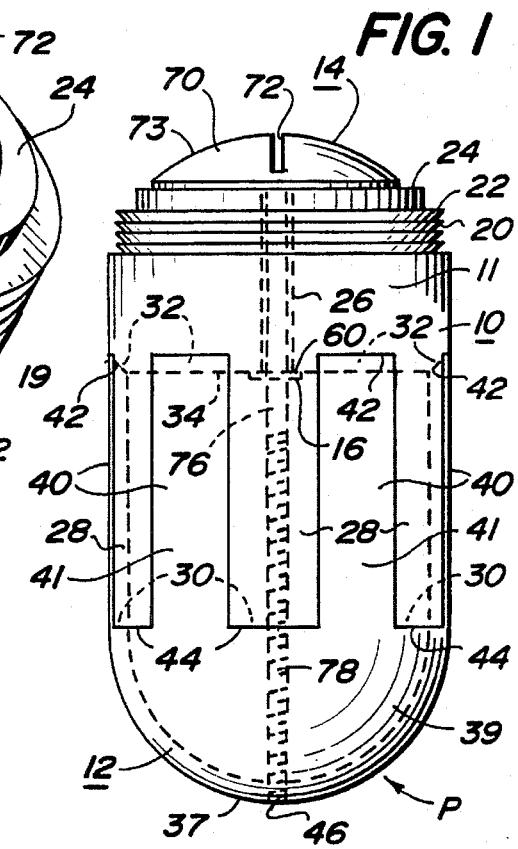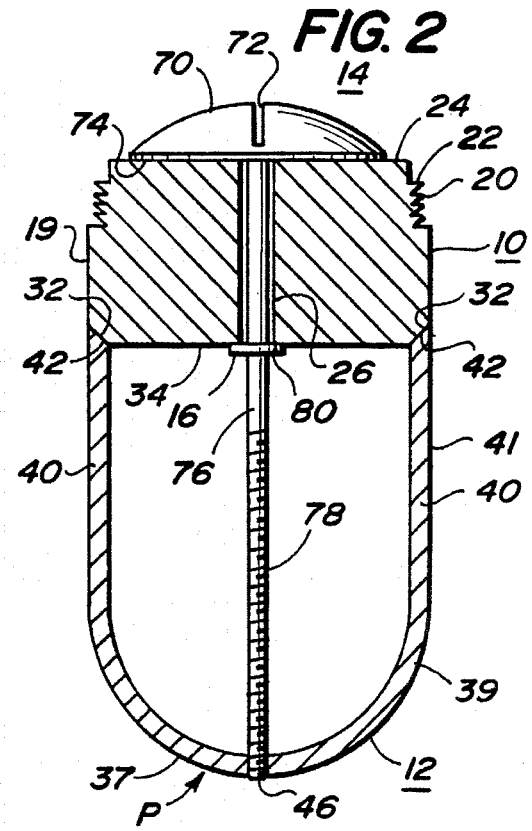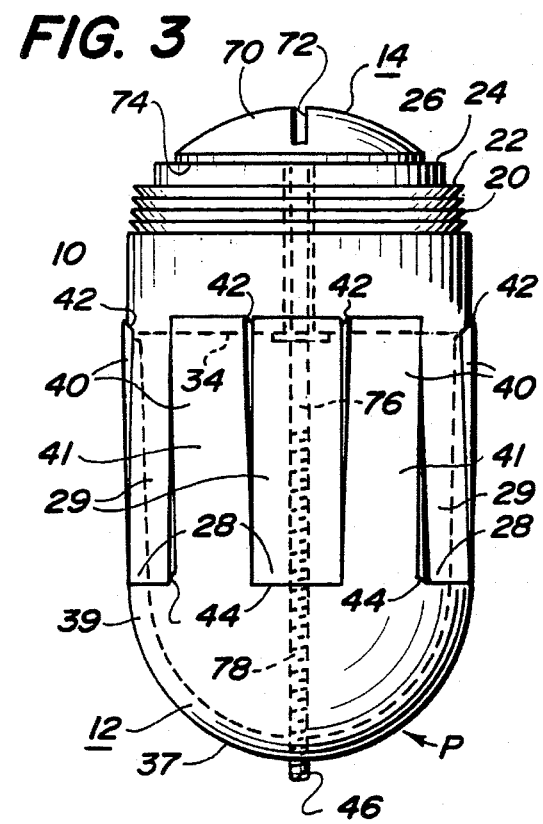

BONE PLUG FIXATION ASSEMBLY, EXPANSIBLE PLUG ASSEMBLY THEREFOR, AND METHOD OF FIXATION

FIELD OF THE INVENTION

The disclosed invention relates generally to surgical implements used in arthroscopic surgery, and more particularly to a bone expansion plug assembly for use in securing ligaments to surrounding bone while the ligament grafts itself to the bone.

BACKGROUND OF THE INVENTION

The repair of the anterior cruciate ligament of the knee necessitates a bone-tendon-bone graft. One bone end of the bone-tendon-bone graft is placed in a drilled hole in the femoral cortex, and the other bone end of the bone-tendon-bone graft is placed in a drilled hole in the interior tibial cortex. The bone portions of the graft are traditionally fixated to the bone with interference screws threadedly secured into the bone. Alternatively, the bone graft can be distally fixated by forming a shallow trough in the anterior tibial cortex so that sutures may secure the graft to a fixation post distally.

The traditional fixation techniques suffer from a number of drawbacks and limitations. For example, the interference screw has a sharp point and may damage the bone during insertion. Also, the screw threads may cut the bone while being threaded into the bone to stabilize the graft. Damage caused by insertion of the interference screw may lead to later problems with the bone. Securing the bone graft with wires likewise suffers from drawbacks because the wires protrude beyond the trough formed in the cortex.

Those skilled in the art will appreciate that there is a need for an assembly which may be readily installed for stabilizing a bone-tendon-bone graft into the surrounding bone, while also minimizing the possibility of the bone becoming damaged during insertion. There is likewise a need for an assembly holder which is easy to manipulate, securely grasps the assembly in order to facilitate manipulation of the assembly, and readily seizes the assembly in order to permit its removal if required. The disclosed invention is just such an assembly and assembly holder and achieves the advantages and overcomes the disadvantages of the prior art through use of an expansible plug. The expansible plug of the invention has a gently rounded insertion end, no protrusions during insertion, and yet may be expanded by and secured to a removable holder.

OBJECTS AND SUMMARY OF THE INVENTION

It is an object of the present invention to provide an expansible plug assembly in which the plug assembly may be expanded radially outwardly to secure relatively soft bone of a graft to the surrounding bone so that the graft is fixated within the drilled bone hole.

It is another object of the present invention to provide an expansible plug assembly which has a smooth outer surface, when in a non-expanded condition, to prevent damage to the bones during insertion of the plug assembly.

It is another object of the invention to provide a plug holder which utilizes a jam rod to positively secure the plug assembly to the plug holder so that the plug assembly and plug holder may be readily manipulated.

It is yet another object of the present invention to provide an expansible plug assembly and plug holder which are simple in construction, effective in use, and economical to manufacture.

An expansible plug assembly pursuant to the present invention comprises a first member closed at one end thereof and having a cylindrical outer surface, a central bore therethrough, and a plurality of longitudinally directed radially extendable fingers. A second member is closed at one end thereof, has a cylindrical outer surface, and a plurality of longitudinally directed radially extendable fingers. The second member fingers are interdigitated with the first member fingers and bear against the first member, and the first member fingers bear against the second member. An axially extensible and retractable compression member extends through the bore and is engaged with the second member for causing the first and second members to be drawn together when the compression member is retracted so that the fingers of the first and second members are thereby caused to extend radially.

A fixation assembly for an expansible bone plug comprises a longitudinally extending outer member, a longitudinally extending inner member, and a driving member. The outer member has an aperture therethrough defining an inner wall with spaced first and second end portions. Threads are formed about the outer member for receiving cooperating threads of a bone plug. A longitudinally extending rod has first and second spaced end portions, and the rod is receivable in the aperture for permitting the first end portion thereof to engage the plug. Means are operably associated with said outer member for locking the rod in engagement with the plug so that movement of the plug relative to the threads is prevented. Means are operably associated with the rod for causing the plug to be expanded.

A method of securing a bone-tendon-bone graft into surrounding bone through use of an expansible bone plug comprises the steps of providing an expansible bone plug having first and second cooperating expansible confronting members. Each member has a plurality of longitudinally directed radially extensible fingers, and the fingers of the first and second members are interdigitated. An opening is formed in the bone. One end of a bone-tendon-bone graft is placed into the opening. The bone plug is positioned in the opening in juxtaposition with the one end of the bone-tendon-bone graft. The fingers of the first and second members are caused to extend radially, thereby securing the one end of the bone-tendon-bone graft within the opening.

These and other objects of the present invention will become apparent from the following detailed description and independent claims.

The invention may be best understood with reference to the accompanying drawings wherein an illustrative embodiment is shown.

BRIEF DESCRIPTION OF THE DRAWINGS

FIG. 1 is an elevational view of the expansible bone plug assembly of the invention in a non-expanded condition with portions shown in phantom;

FIG. 2 is a cross sectional view of the bone plug assembly of FIG. 1;

FIG. 3 is an elevational view of the bone plug assembly of FIG. 1 in an expanded condition;

FIG. 4 is a perspective view of the bone plug assembly of the invention in the expanded condition;

DETAILED DESCRIPTION OF THE INVENTION

Figure 6:
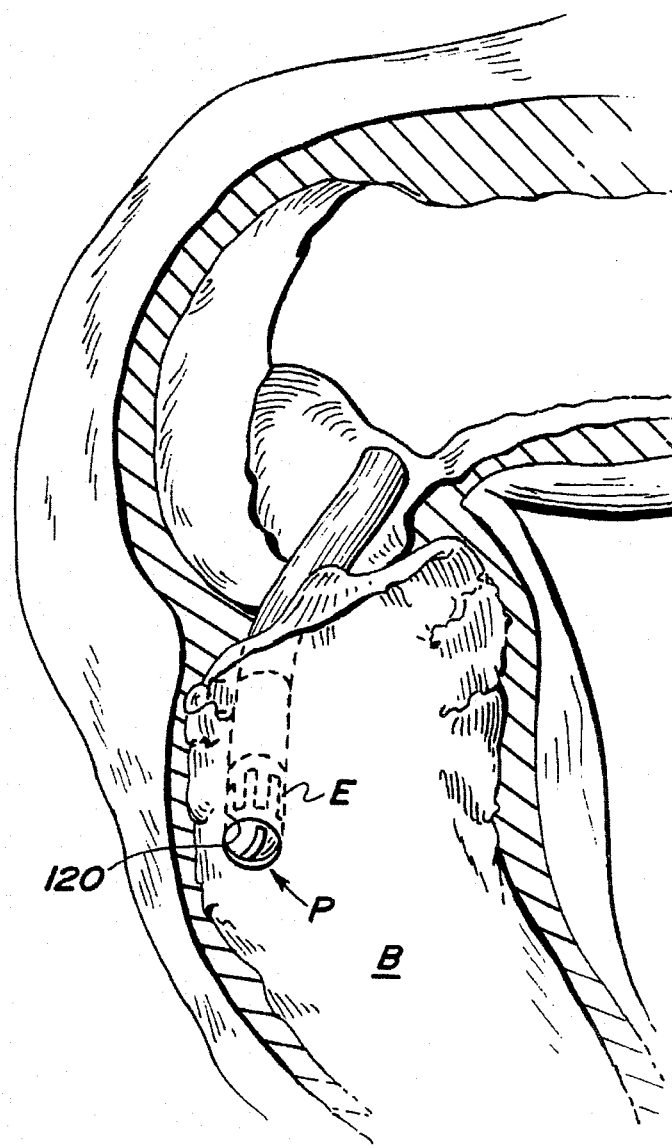
FIG. 6 is a perspective view with portions broken away and partially in section disclosing the bone plug assembly of FIG. 1 inserted into a bone and securing a bone-tendon-bone graft thereto.

Expansible plug assembly P, as best shown in FIGS. 1–4, has a first member 10, a confronting second member 12, a threaded member 14, and a C-clip 16 longitudinally securing threaded member 14 relative to first member 10. First and second members 10 and 12, respectively, may be oriented into a first non-expanded condition, as best shown in FIG. 1, in which plug assembly P is arranged for insertion into or withdrawal from a hole drilled in surrounding bone, and a second expanded condition, as best shown in FIGS. 3 and 4, in which interdigitated fingers extend radially outwardly beyond the outer surface of plug assembly P for engaging the surrounding bone so as to stabilize and fixate a bone-tendon-bone graft thereto, as best shown in FIG. 6.

For convenience, the present invention will be described in relation to the orientation shown in FIGS. 1–5, and consequently terms such as "above", "upwardly", and "bottom", etc., as used herein, are to be construed in the relative sense, and it shall be understood that expansible plug assembly P and plug holder H are capable of being used in any orientation.

First member 10, as best shown in FIG. 1, has a smooth outer cylindrical surface 19. The outer diameter of member 10 may range from 4–10 mm, preferably from 6–8 mm. First member 10 is constructed of surgical grade titanium. A first set of threads 20 is disposed about the upper end of member 10. Threads 20 preferably are left hand threads. Threads 20 do not extend radially beyond outer cylindrical surface 19, and preferably are inwardly disposed relative to surface 19. First upwardly projecting surface 22 extends radially above threads 20 and provides a shoulder. A second surface 24 projects longitudinally from and is formed above surface 22. The outer diameter of surface 24 is the same as the inner diameter of surface 22, and thereby provides a second shoulder. Aperture 26 is centrally disposed in first member 10 and extends therethrough from surface 24 which effectively closes one end of member 10.

Six circumferentially spaced longitudinally directed fingers 28 extend axially from collar 11 of member 10. Each finger 28 has an arcuate contour conforming to surface 19 when in the non-expanded condition, as best shown in FIG. 1. The fingers 28 are approximately 30° in arc length. While six fingers 28 are effective, those skilled in the art will understand that the number may be varied.

As best shown in FIG. 1, the outer surface 29 of each finger 28 has approximately the same outer diameter as that of cylindrical surface 19, and each finger 28 extends the same distance axially from collar 11. Beveled surface 30, as best shown in FIG. 4, is formed at the distal end of each of fingers 28. A correspondingly beveled surface 32 is disposed between fingers 28 at the proximal ends thereof along collar 11. Surface 34 extends radially inwardly from fingers 28, as best shown in FIG. 2, at the distal end of collar 11.

Second member 12 has a smooth outer cylindrical surface 39 which, when plug assembly P is assembled, is concentric with outer surface 19 and of approximately the same diameter. Second member 12 is also constructed of surgical grade titanium. One end of second member 12 has a gently rounded surface 37 providing an insertion end for assembly P and closing the end thereof. Circumferentially spaced longitudinally directed fingers 40 extend from surface 37 and are interdigitated with fingers 28. Fingers 40 have a uniform length, and fingers 40 each subtend an angle corresponding to the angle disposed between fingers 28 of first member 10. In this way, plug P is an essentially closed structure when in the unexpanded orientation of FIG. 1. Threaded bore 46 is formed in surface 37, which closes one end of member 12, for receiving threaded member 14.

Each finger 40 has an outer surface 41 of approximately the same outer diameter as surface 29. Each finger 40 has a beveled distal end surface 42 in abutting relation with an associated beveled surface 32 of first member 10. A beveled surface 44, with an arc length of approximately 30°, is disposed at the proximal end of each finger 40 in surface 37. Each beveled edge 30 of fingers 28 is brought into abutting relation with the cooperating beveled surface 44 of second member 12 when plug P is assembled.

Threaded member 14, as best shown in FIGS. 1 and 2, has a head portion 70 of a larger diameter than aperture 26 and is adapted for bearing upon surface 24. Threaded member 14 is constructed of surgical grade stainless steel or from surgical grade titanium. Head portion 70 has a slot 72, an upper arcuate surface 73, and a flat bottom surface 74. Those skilled in the art will recognize that other headed screw configurations may be substituted for the slotted head disclosed herein. Integral with head portion 70 is an elongated shaft 76 which has a threaded distal portion 78. Shaft 76 extends through smooth bore aperture 26 and threaded portion 78 is received in threaded hole 46. An annular groove 80 is formed in shaft portion 76 and a C-clip 16 is snap-fit into groove 80 to secure threaded member 14 to first member 10. C-clip 16 is constructed of a surgical grade stainless steel.

Figure 5:
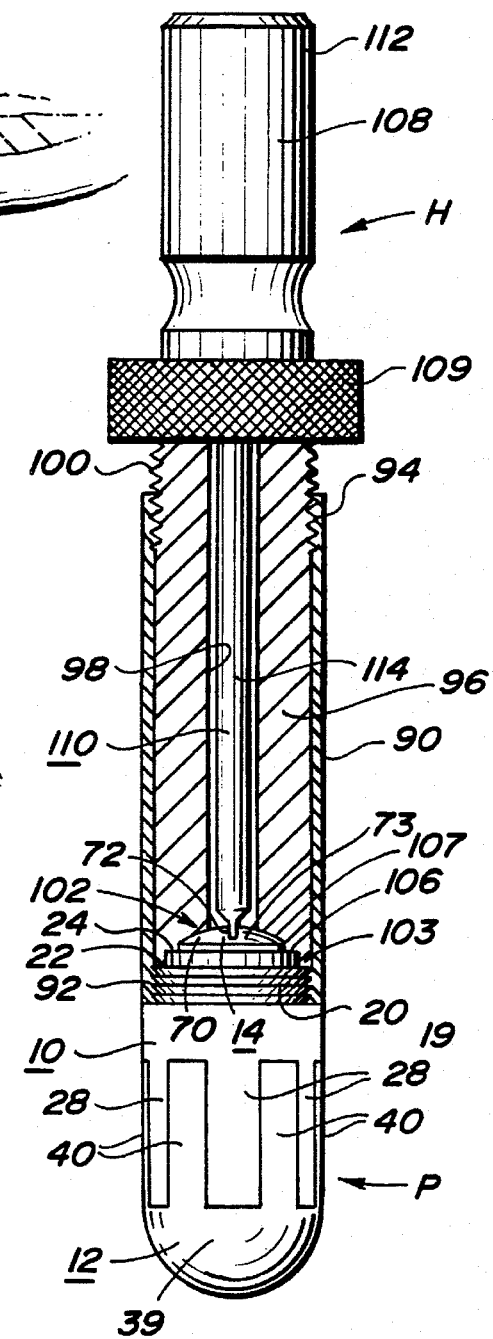
FIG. 5 is an elevational view partially in section of the bone plug assembly secured to the plug holder assembly of the invention.

Plug holder assembly H, as best shown in FIG. 5, has an outer elongated tubular sleeve 90, with a lower internally threaded portion 92, and an internally threaded upper portion 94. Threaded portion 92 has left hand threads to cooperate with threads 20 about plug P to which it is secured.

Elongated cylindrical jam sleeve or rod 96 is slidably received in outer sleeve 90, and has a central bore 98 extending therethrough. Jam sleeve 96 has an upper threaded portion 100 which cooperates with upper threaded portion 94 of outer sleeve 90. Jam sleeve 96 has a shoulder 102 formed at its distal end. Shoulder 102 has a large diameter portion 103 providing a downwardly projecting surface. Flat downwardly projecting surface 106 is formed radially inwardly and above the flat surface of portion 103. Concave surface 107 is formed above surface 103 and conforms generally to the curvature of surface 73 of threaded member or screw 14, but is sized so as to not contact surface 73 when jam sleeve 96 engages first member 10 through surfaces 163 and 106.

Knurled portion 109 is formed on an opposite end of jam sleeve 96, and has a diameter larger than that of outer sleeve 90 to facilitate being grasped and rotated by the surgeon. The relatively large diameter of knurled portion 109 supplies mechanical advantage so that only light finger pressure is necessary to rotate jam sleeve 96 so that surfaces 103 and 106 will engage the confronting surfaces 22 and 24, respectively, of first member 10.

Screwdriver 108 has a driver portion 110 with a blade receivable within slot 72 of threaded member 14, a handle portion 112, and an elongated shaft 114. Elongated shaft 114 and driver portion 110 extend through bore 98 and are freely rotatable therein.

To assemble plug assembly P, shaft 76 is positioned within aperture 26 of first member 10 and C-clip 16 installed about groove 80. Fingers 40 of second member 12 are brought into interdigital orientation relative to fingers 28 of first member 10, and threaded member 14 is rotated so that threaded portion 78 engages bore 46. Threaded portion 78 is rotated within bore 46 so as to snugly fit beveled surfaces 42 against 34 and beveled surfaces 30 and 44, but not so much as to cause members 10 and 12 to be drawn together and fingers 28 and 40 to thereby be moved or extended radially outwardly. Plug assembly P is thus in the non-expanded condition, suitable for insertion into a previously drilled hole in a bone.

To secure plug holder H to plug assembly P, as best shown in FIG. 5, lower threaded portion 92 is engaged with threads 20 of first member 10. Jam sleeve 96 is then positioned within outer sleeve 90, and upper threaded portion 94 is threadedly engaged with upper threaded portion 100. Threads 94 and 100 cooperate so that jam sleeve 96 may be advanced or retracted relative to surfaces 22 and 24 by appropriate rotation of jam sleeve 96. FIG. 5 discloses surfaces 103 and 106 engaged with either surfaces 22 and 24, respectively. Jam sleeve 96 exerts sufficient force on first member 10 to lock the threads 20 and 92 together, thereby preventing rotation of plug assembly P relative to outer sleeve 90 and jam sleeve 96.

After plug P and holder H have been secured together, screw driver 108 is attached. The blade of driver portion 110 is aligned and engaged with slot 72. Rotation of head 70 in one direction causes first and second members 10 and 12 to be drawn together, so that fingers 28 and 40 spread radially outwardly from surfaces 19 and 39 into the expanded condition as a result of the cooperating beveled surfaces 32 and 42 and 30 and 44. Conversely, rotation of threaded member 14 in the opposite direction causes first and second members 10 and 12 to be moved apart, so that fingers 28 and 40 move radially inwardly from the expanded condition to the non-expanded condition. Because of the camming surfaces provided by the beveled ends, then the fingers 28 and 40 may relatively easily be radially moved by rotation of screw 14.

The locking force applied to plug assembly P by jam sleeve 96 is sufficient to prevent rotation of plug assembly P relative to plug holder H when screwdriver 108 and threaded member 14 are rotated while installing plug assembly P in the surrounding bone.

The radial expansion of fingers 28 and 40 corresponds to the number of revolutions of threaded member 14. A 2 mm to 3 mm increase in the diameter of fingers 28 and 40 at their distal ends relative to the non-expanded condition should provide adequate securement of plug assembly P when installed as illustrated in FIG. 6.

As best shown in FIG. 6, opening 120 is drilled or otherwise formed in bone B. One end E of bone-tendon-bone graft L is positioned within opening 120. The bone of the one end E is relatively soft and compressible, and needs to be fixated in order to permit the graft to ultimately be secured to bone B. Because of the softness and compressibility of one end E, then plug assembly P may also be positioned within opening 120. Bone plug P compresses the bone material of end E against the wall of the opening 120, thereby minimizing tendency of the bone of end E to move within opening 120. Expansion of fingers 28 and 40 will cause those fingers at their distal ends to engage the wall of opening 120, thereby precluding end E from moving axially within opening 120. Because the beveled surfaces 30 and 42 extend in opposite directions, then plug assembly P and the bone of end E are thus fixed within opening 120.

Should plug assembly P need to be removed from the surrounding bone B, then this may be accomplished essentially by the reverse of its installation. C-clip 16 facilitates removal by engaging bottom facing surface 34 as threaded member 14 is rotated in a direction opposite to the installation direction. Threaded member 14 pushes second member 12 away from first member 10, so that fingers 28 and 40 retract radially inwardly. While I disclose screw 14 for drawing members 10 and 12 together, those skilled in the art will appreciate that other types of axially extensible means may be provided to draw members 10 and 12 together, or to cause them to move apart.

It should be appreciated that plug assembly P provides smooth essentially uninterrupted surfaces 19, 29, and 37 which permit plug assembly P to be inserted and installed with minimal damage, if any, to the surrounding bones B and E. The construction of plug assembly P permits fingers 28 and 40 to extend gradually radially outwardly, thereby reducing the risk of overstressing the surrounding bone. The bone portion E of the bone-tendon-bone graft L is soft, and so will conform to the available space between the surrounding bone and installed plug assembly P. Compressing the soft bone tissue by expansion of plug assembly P causes the soft bone tissue to be secured and fixed within the bone portion of the surrounding bone.

It will be appreciated that the plug assembly P and the holder H form an integral device, with the plug P being held against rotation relative to the holder H. As a result, manipulation of plug assembly P can be carried out by using holder H and plug P as a single unit.

While this invention has been described as having a preferred design, it is understood that it is capable of further modifications, uses/or adaptations, following in general the principle of the invention, and including such departures from the present disclosure as have come within known or customary practice in the art to which the invention pertains, and as may be applied to the central features hereinbefore set forth, and fall within the scope of the invention of the limits of the appended claims.

What is claimed is:

1. An expansible bone plug assembly, comprising:

a) a first member closed by a substantially planar surface at one end thereof and having a cylindrical outer surface, a central bore through said planar surface and a plurality of longitudinally directed radially extendable fingers;

b) a second member closed by a hemispherical surface at one end thereof and having a cylindrical outer surface, and a plurality of longitudinally directed radially extendable fingers, said second member fingers being interdigitated with said first member fingers and bearing against said first member and said first member fingers bearing against said second member;

c) an axially extensible and retractable compression member extending through said bore and engaged with said second member and causing said first and second members to be drawn together when said compression member is retracted so that said fingers of said first and second members are thereby caused to extend radially outwardly; and d) threads extend about said first member one end for threaded engagement with a manipulator, said threads being radially inwardly spaced relative to said first member outer surface.

2. The assembly of claim 1, wherein:
a) said fingers of said first and second members have a common length.

3. The assembly of claim 1, wherein:
a) said fingers of said first and second members are equiangularly spaced.

4. The assembly of claim 3, wherein:
a) each of said fingers of said first and second members has a distal beveled end bearing against the confronting member.

5. The assembly of claim 4, wherein:
a) each of said first and second members has a beveled portion; and
b) the beveled ends of the fingers of said first and second members bear against the beveled portions of the juxtaposed said first and second members.

6. The assembly of claim 1, wherein:
a) said compression member is a threaded screw; and
b) said second member has a threaded bore receiving an end portion of said screw so that rotation of said screw in a preselected direction causes retraction thereof and rotation of said screw in an opposite preselected direction causes extension thereof.

7. The assembly of claim 6, wherein:
a) said first member bore is smooth; and
b) means extend about said screw for securing said screw to said first member.

8. The assembly of claim 7, wherein:
a) said screw has a head resting upon said first member and a shank extending through said bore into said opening;
b) said shank is threaded along a portion of the length thereof and has an unthreaded portion; and
c) said securing means are disposed about said unthreaded portion.

9. The assembly of claim 1, wherein:
a) a portion of the periphery of said first member is threaded.

10. The assembly of claim 9, wherein:
a) said bore is disposed centrally within said first member.

11. The assembly of claim 1, wherein:
a) a threaded bore is formed in said second member hemispherical surface for receipt of an end portion of said compression member;
b) said first member central bore is smooth;
c) said compression member has a threaded portion received with said threaded bore, and a smooth portion received within said central bore; and
d) means are operatively disposed about said smooth portion for maintaining said compression member relative to said first member.

12. The assembly of claim 11, wherein:
a) said compression member has a groove disposed in said smooth portion; and b) said maintaining means is received with said groove.

13. The assembly of claim 12, wherein:
a) said maintaining means is a C-clip.

14. Expansible bone plug for surgical implantation, comprising:
a) a first member closed at one end by a thread bearing shouldered end unit and having a cylindrical outer surface, a central bore through said end unit, and a plurality of longitudinally directed radially extendable fingers;
b) a second member closed at one end by a hemispherical surface and having a cylindrical outer surface, and a plurality of longitudinally directed radially extendable fingers, said second member fingers interdigitated with said first member fingers and bearing against said first member and said first member fingers bearing against said second member;
c) an axially extending compression member extending through said bore and engaged with said second member for causing said members to be drawn together and the fingers of said first and second members to be radially extended;
d) means disposed about said compression member for longitudinally securing said compression member relative to said first member;
e) the threads of said end unit are radially inwardly spaced relative to said first member cylindrical surface; and
f) said end unit inculcates a first planar surface and a second axially spaced planar surface, the threads of said end unit being interposed between said planar surfaces.

15. The bone plug of claim 14, wherein:
a) said bore is smooth;
b) a threaded opening extends through said hemispherical surface coaxial with said bore;
c) said compression member includes a head bearing upon said first planar surface, a smooth shank portion extending through said bore, and a threaded shank portion received with said threaded opening so that rotation of said compression member causes said first and second members to move relative to each other and thereby the fingers thereof to assume a radially selected position; and
d) said maintaining means are disposed about said smooth shank portion.

16. The bone plug of claim 15, wherein:
a) a third planar surface is axially spaced from said second planar surface, and said maintaining means is positioned proximate said third surface.

17. The bone plug of claim 14, wherein:
a) there are at least six fingers equiangularly disposed about each of said first and second members, each finger subtending an arc of substantially 30°; and
b) each finger has a proximal end portion and a beveled distal end portion.

* * * * *